(12) United States Patent
Sinha

(10) Patent No.: US 9,234,779 B2
(45) Date of Patent: Jan. 12, 2016

(54) INTEGRATED ACOUSTIC PHASE SEPARATOR AND MULTIPHASE FLUID COMPOSITION MONITORING APPARATUS AND METHOD

(71) Applicant: Los Alamos National Security, LLC, Los Alamos, NM (US)

(72) Inventor: Dipen N. Sinha, Los Alamos, NM (US)

(73) Assignee: LOS ALAMOS NATIONAL SECURITY, LLC, Los Alamos, NM (US)

( * ) Notice: Subject to any disclaimer, the term of this patent is extended or adjusted under 35 U.S.C. 154(b) by 0 days.

(21) Appl. No.: 14/142,489

(22) Filed: Dec. 27, 2013

(65) Prior Publication Data

US 2014/0109684 A1  Apr. 24, 2014

Related U.S. Application Data

(62) Division of application No. 13/225,734, filed on Sep. 6, 2011, now Pat. No. 8,640,529.

(60) Provisional application No. 61/379,864, filed on Sep. 3, 2010.

(51) Int. Cl.
*G01F 15/02* (2006.01)
*G01F 1/74* (2006.01)
(Continued)

(52) U.S. Cl.
CPC .............. *G01F 1/74* (2013.01); *B01D 19/0078* (2013.01); *E21B 47/101* (2013.01); *G01F 1/66* (2013.01); *G01F 1/667* (2013.01); *G01F 1/668* (2013.01); *G01F 1/712* (2013.01); *G01F 15/02* (2013.01);
(Continued)

(58) Field of Classification Search
USPC .............. 73/61.44, 61.45, 61.61, 19.01, 19.1, 73/19.12; 95/30, 241
See application file for complete search history.

(56) References Cited

U.S. PATENT DOCUMENTS 4,083,225 A * 4/1978 Day et al. ...................... 73/19.03
4,168,295 A * 9/1979 Sawyer .......................... 422/111
(Continued)

FOREIGN PATENT DOCUMENTS

JP       2870370 B2 *   3/1999

OTHER PUBLICATIONS

English Abstract of JP 2870370 Mar. 1999.*
(Continued)

*Primary Examiner* — Peter Macchiarolo
*Assistant Examiner* — Alexander Mercado
(74) *Attorney, Agent, or Firm* — Samuel M. Freund; Cochran Freund & Young LLC

(57) ABSTRACT

An apparatus and method for down hole gas separation from the multiphase fluid flowing in a wellbore or a pipe, for determining the quantities of the individual components of the liquid and the flow rate of the liquid, and for remixing the component parts of the fluid after which the gas volume may be measured, without affecting the flow stream, are described. Acoustic radiation force is employed to separate gas from the liquid, thereby permitting measurements to be separately made for these two components; the liquid (oil/water) composition is determined from ultrasonic resonances; and the gas volume is determined from capacitance measurements. Since the fluid flows around and through the component parts of the apparatus, there is little pressure difference, and no protection is required from high pressure differentials.

9 Claims, 12 Drawing Sheets

(51) Int. Cl.
*G01F 1/66* (2006.01)
*B01D 19/00* (2006.01)
*G01N 29/032* (2006.01)
*G01N 29/036* (2006.01)
*E21B 47/10* (2012.01)
*G01F 1/712* (2006.01)
*G01N 29/024* (2006.01)

(52) U.S. Cl.
CPC ............ *G01F 15/024* (2013.01); *G01N 29/024* (2013.01); *G01N 29/032* (2013.01); *G01N 29/036* (2013.01); *G01N 2291/024* (2013.01)

(56) References Cited

U.S. PATENT DOCUMENTS

| | | | | |
|---|---|---|---|---|
| 4,339,247 | A * | 7/1982 | Faulkner et al. | 95/30 |
| 5,395,592 | A * | 3/1995 | Bolleman et al. | 422/128 |
| 5,533,402 | A | 7/1996 | Sarvazyan et al. | |
| 5,596,150 | A * | 1/1997 | Arndt et al. | 73/861.12 |
| 6,497,140 | B1 * | 12/2002 | Zeqiri | 73/61.61 |
| 8,128,730 | B2 * | 3/2012 | Williamson | 95/30 |
| 8,382,886 | B2 * | 2/2013 | Kelly | 96/175 |
| 2002/0162393 | A1 * | 11/2002 | Kaduchak et al. | 73/570.5 |
| 2005/0000289 | A1 | 1/2005 | Gysling et al. | |
| 2005/0097943 | A1 * | 5/2005 | Sinha | 73/61.49 |
| 2009/0178716 | A1 * | 7/2009 | Kaduchak et al. | 137/13 |
| 2013/0047709 | A1 * | 2/2013 | Xie et al. | 73/61.45 |

OTHER PUBLICATIONS

Derwent Entry for JP 2870370 Mar. 1999.*
"Apparatus and Method for Noninvasive Particle Detection Using Doppler Spectroscopy," by Dipen N. Sinha, filed on Sep. 6, 2011.
International Search Report, International Searching Authority, Dec. 23, 2011, pp. 1-15.
"Method for Noninvasive Determination of Acoustic Properties of Fluids Inside Pipes," by Dipen N. Sinha et al., filed on Sep. 6, 2011.
"The Determination of the Speed of Sound in Liquids Using Acoustic Resonance in Piezoelectric Tubes," by Bogdan V. Antohe and David B. Wallace, Meas. Sci. Technol. 10 (1999) 994-998.

* cited by examiner

US 9,234,779 B2

INTEGRATED ACOUSTIC PHASE SEPARATOR AND MULTIPHASE FLUID COMPOSITION MONITORING APPARATUS AND METHOD

CROSS-REFERENCE TO RELATED APPLICATIONS

The present application is a divisional application of U.S. patent application Ser. No. 13/225,734, for "Integrated Acoustic Phase Separator and Multiphase Fluid Composition Monitoring Apparatus," which was filed Sep. 6, 2011, which application claims the benefit of U.S. Provisional Patent Application No. 61/379,864 for "Integrated Acoustic Phase Separator And Multiphase Fluid Composition Monitoring Device" which was filed on Sep. 3, 2010. The entire contents of both applications are hereby specifically incorporated by reference herein for all that they disclose and teach.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to an apparatus and method for determining the properties of a multiphase fluid containing at least two liquid phases and a gaseous phase and, in particular, embodiments of the invention permit the separation of the gas and liquid phases and the measurement of the volume and composition of each phase.

BACKGROUND OF THE INVENTION

Fluid from oil wells generally includes a mixture of gas, produced water and hydrocarbon (crude oil). The real-time determination of the actual quantity of oil produced in a given well is necessary for the determination of royalties in the oil production industry. Presently, there are several methods for accomplishing such metering. As an example, the fluid stream from a well may be sent to a separation tank where it can separate by gravitational forces after which relative amounts of the various phases may be determined. However, many hours are required for this separation, and large tanks are employed. The density of heavy crude is approximately the same as that for water and separation is difficult without heating the fluid. Once heated, the densities of oil and water are sufficiently different to permit gravitational separation, but significant energy is wasted in the heating process.

Another procedure includes a phase separator, for example, a cyclone separator, for separating gas from the fluid stream. A large mechanical piping system external to the pipe carrying the mixed fluid stream is required. Once the gas is separated from the fluid, a microwave-based liquid/liquid analyzer (for example, the OW-200 series system by Agar Corporation), as an example, can be used to determine the oil-water composition. This procedure is effective for heavy crude, but in the case of light crude, more accurate density measuring devices, such as Coriolis-type meters (for example, the Coriolis meter by MicroMotion Elite) system may be used to determine the density of the oil-water mixture from which the fluid composition can be determined. Measurement systems having such capabilities are large and expensive and, as a result, it is often not possible to include such devices at every well. The flow streams from multiple wells are therefore often combined and measurements are made on the combined flow stream, which makes it difficult to determine the output of individual wells without switching the individual flow streams to the measurement device. Difficulty and expense of such measurements increases if monitoring needs to be accomplished significantly below the surface or in a deep sea operation.

If the flow stream needs to be monitored at various perforation levels in a well to determine which perforation levels are producing valuable fluids and which of the remaining levels should be closed down, a device must be lowered into the well to make this measurement. Borehole TV cameras and infra-red detectors have been used, but with limited success. Additionally, these procedures do not provide quantitative measurements of fluid composition down hole.

SUMMARY OF THE INVENTION

Embodiments of the present invention overcome the disadvantages and limitations of the prior art by providing a logging tool that can be moved through production zones in a well and continuously monitor fluid composition in the wellbore.

It is another object of embodiments of the invention to provide a logging tool for continuously monitoring fluid composition in a wellbore, wherein the fluid is flowing.

It is further an object of embodiments of the present invention to provide an apparatus for separating gas from the fluid in a wellbore, determining the quantities of the individual fluid components, and permitting the components to remix without affecting the fluid flow in the wellbore.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for determining properties of a multiphase fluid comprising a liquid having at least one component and a gas, hereof, includes: a first hollow piezoelectric cylinder having a first axis, an inside wall and an outside wall, wherein the inside wall comprises a first electrode and the outside wall comprises a second electrode; a first signal generator for providing a first chosen electrical signal to one of the first electrode or the second electrode, the other of the first electrode and the second electrode being grounded, whereby the gas is separated from the multiphase fluid flowing through the first hollow piezoelectric cylinder; a second hollow piezoelectric cylinder having a second axis collinear with the axis of the first hollow piezoelectric cylinder, wherein the inside wall of the second cylinder comprises a grounded third electrode, and the outside wall of the second cylinder comprises at least two diametrically opposed fourth electrodes; a second signal generator for providing a second chosen electrical signal to one of the at least two fourth electrodes, wherein resonant acoustic vibrations are generated in the at least one component; and a gain-phase measurement circuit for comparing the signal from the first signal generator with signals received by the second of the at least two fourth electrodes, wherein the phase difference between the generated signal and the received signal and the amplitude of the received signal are determined; whereby the speed of sound in the at least one component and the sound attenuation in the at least one component are determined, from which the composition of the at least one component from which the gas has been separated is determined by acoustic interferometry.

In another aspect of the present invention and in accordance with its objects and purposes, the method for determining properties of a multiphase fluid comprising a liquid having at least one component and a gas, hereof, includes: generating radial acoustic radiation forces in a first hollow piezoelectric cylinder having an axis, through which the multiphase fluid is caused to flow, such that the gas is directed away from the axis thereof and separated from the liquid; and measuring the sound speed and sound attenuation of the at least one component from which the gas has been separated; whereby the composition of the at least one component is determined.

Benefits and advantages of embodiments of the present invention include, but are not limited to, providing an apparatus and method for separating the gaseous from the liquid constituents and for determining and monitoring the composition of a multiphase fluid, which may be used in a high-pressure environment, such as deep boreholes in oil producing wells since the fluid may flow both outside and inside of a hollow cylindrical apparatus support such that there is little pressure difference, permitting fragile crystal resonator sensors to be used, whereas other known techniques require rugged systems or protection of the sensors from high-pressure differentials.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 11A shows capacitance measurements in water without any air bubbles, while FIG. 11B shows the measurement with air inside the apparatus.

DETAILED DESCRIPTION OF THE INVENTION

Figure 1:
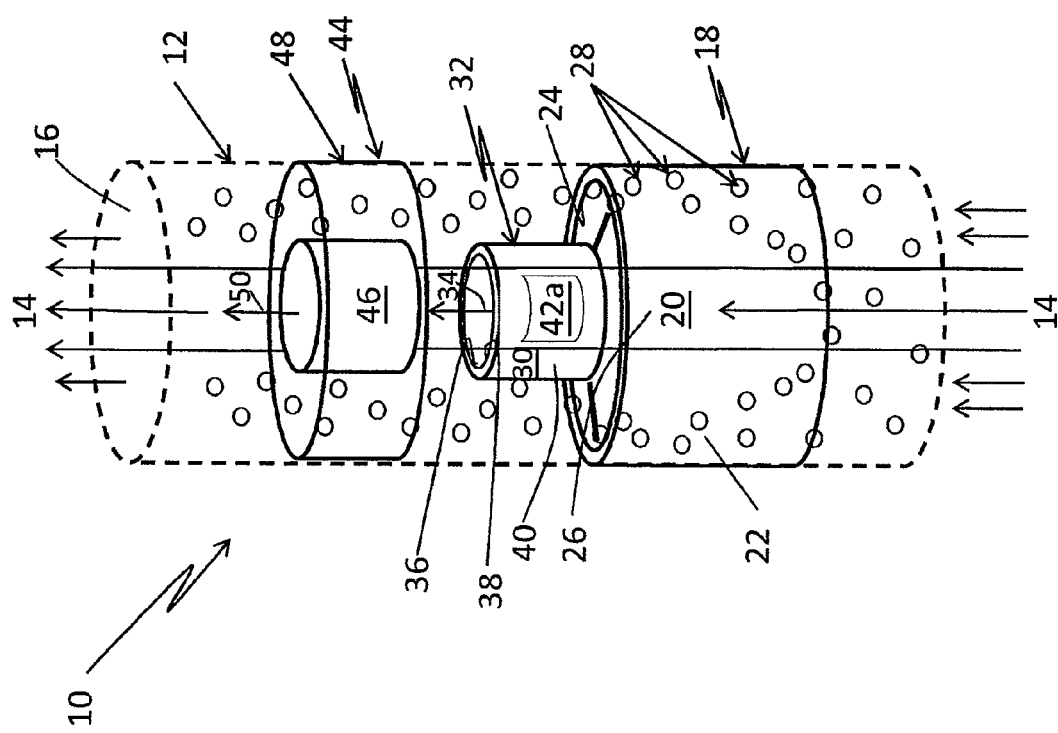
FIG. 1 is a schematic representation of a perspective view of an embodiment of the combined acoustic phase separator and multiphase fluid composition monitor of the present invention.

Briefly, embodiments of the present invention include an apparatus which may be lowered down hole for separating gas from the multiphase fluid flowing in a wellbore or a pipe, determining the quantities of the individual components in the resulting liquid which comprises at least one component, and permitting the gas to remix with the liquid after which the gas volume may be measured, without affecting the flow stream. Acoustic radiation forces are employed to separate gas from the liquid, thereby permitting measurements to be made for the at least one component; the liquid (oil/water) composition is determined from ultrasonic resonances; and the gas volume is determined from capacitance measurements. The equations set forth hereinbelow are valid for both immiscible liquids and solutions.

An embodiment of the apparatus for determining properties of a multiphase fluid, includes a first hollow piezoelectric cylinder for separating the gas from the liquid; and a second hollow piezoelectric cylinder, downstream therefrom for determining and monitoring the composition of the liquid after the majority of the gas present in the fluid has been removed. The volume of gas after recombination with the liquid may be determined by a capacitance measurement using a pair of concentric hollow metal cylinders downstream from the second piezoelectric cylinder. A temperature sensor for measuring the temperature of the multiphase fluid permits correction of the measurements for variations in temperature.

In use, the apparatus of the present invention determines the properties of a multiphase fluid which includes a liquid and a gas, wherein the liquid has at least one component, including directing the fluid into an acoustic phase separator, wherein the gas is separated from the liquid using acoustic radiation forces, and determining the composition of the at least one component. A first component may be oil, a second component may be water, and the gas may be a hydrocarbon. The step of determining the composition of the first and second components may include measuring the sound speed and sound attenuation of the first and second components of the liquid in the absence of the gas, and measuring the temperature of the liquid to correct the sound speed in the liquid for variation with temperature. A step of measuring the volume of the gas may include remixing the gas and the liquid, and measuring the capacitance using a concentric capacitance cell. The flow rate of the liquid may also be measured.

Although an acoustical procedure for releasing dissolved gas in a fluid in the form of bubbles is described by Faulkner et al. in U.S. Pat. No. 4,339,247, rectified diffusion is employed in a process similar to cavitation. By contrast, the present invention directs gas bubbles already present in the fluid in the form of a multiphase mixture, away from the composition analysis elements of the invention.

A volume of one fluid within a host fluid that is dissimilar in density and compressibility experiences a differential force if the fluid is put inside a resonator cavity and a standing wave pattern is created. The force may be expressed as $$F_{ac} = \left[\frac{P_0^2 V_p \beta_m}{2\lambda_m}\right]\varphi(\beta, \rho)\sin\left(\frac{4\pi z}{\lambda_m}\right),$$

where $$\varphi(\beta, \rho) = \left(\frac{5\rho_p - 2\rho_m}{2\rho_p + \rho_m} - \frac{\beta_p}{\beta_m}\right)$$

is called the acoustic contrast factor and $V_p$ is the volume of the particle, droplet or bubble, $\beta$ is the compressibility, $\rho$ is the density, $\lambda$ is the wavelength of sound, $P_0$ is the peak acoustic pressure, z is the distance from pressure node, and m and p are the medium and particle (subscripts), respectively. The acoustic contrast factor $\phi$ can be either positive or negative, which determines the direction of the force. For, solid particles, the acoustic force will push these particles to a standing wave node, whereas a gas bubble will experience an opposite force and be pushed away from the node. This is the force that pushes the gas bubbles toward the inner wall of the cylindrical piezoelectric resonator if the resonator is driven at an appropriate frequency.

A piezoelectric-tube resonator provides a straightforward means for carrying out ultrasonic interferometry on liquids and emulsions. There are no adjustable parts as for parallel plate resonator systems and the tube resonator is self aligned. The relationship between the velocity of sound c and the frequency difference $\Delta f$ between consecutive interference peaks for this cylindrical system is also given by c=2 d $\Delta f$, where $\Delta f$ is the frequency difference between consecutive resonance peaks. Away from the center frequency of the resonator (the thickness mode resonance frequency), the resonance peaks are equally spaced in frequency. It is worth noting that since the geometry of the cylinder is fixed, the resonance spectrum for any given liquid is entirely predictable. Consequently, it is possible to determine sound speed of a liquid simply by tracking the location of a single peak. This makes real-time monitoring of sound speed of a liquid straightforward.

Sound absorption may be determined from the spectra obtained from the piezoelectric cylinder from the broadening of the resonance peaks. Therefore, the full-width-at-half-maximum (FWHM) of the peaks for any liquid is a measure of the sound attenuation in the liquid. As will be discussed in more detail hereinbelow, differences in this value can be readily observed from the data presented where the glycerol peaks are many times broader than that of either water or ethanol. The amplitude of a given peak is also related to the sound attenuation. Thus, two important physical parameters can be easily extracted from this resonance spectrum and these in turn can be related to the oil-water composition.

Advantages of the cylindrical resonator for interferometric fluid measurements include:
1. No mechanical alignment is needed as would be for parallel plate resonators, which require optical quality alignment for good data, because the cylindrical geometry resonator system is always aligned.
2. The cylindrical resonator is constructed from piezoelectric material; therefore no separate container is needed for its operation, and no piezoelectric transducers need to be mounted on any surfaces.
3. Typically two electrodes are etched on opposite sides of the cylinder, which serve as the opposing transducers (transmitter and receiver) in the resonator system (silver paint or other appropriate conductive paint or deposited metal may be used to create the electrodes).
4. It is possible to use only a single electrode for the resonator where the electrical impedance of that electrode is used to monitor the resonances, the opposite wall of the cylinder functioning as a reflector.
5. A significant advantage is the use of this resonator in high-pressure systems, such as deep boreholes in oil producing wells, since the liquid can surround the hollow cylinder, whereby there is no pressure difference, which allows operation with fragile crystal resonator systems.

Gas volume may be determined by a capacitance measurement using two concentric metal cylinders. The central cylinder is the central electrode of a capacitor and is closed on both ends to prevent liquid from passing through it and disturbing the gas volume measurement since the bubbles passing through the central electrode would not be measured. The diameter of this cylinder is not critical, and in an embodiment of the present apparatus the diameter was chosen to be the same as the diameter of the piezoelectric-tube resonator described hereinabove. In an embodiment of the present invention, the outer electrode was chosen to have the same diameter as the acoustic phase separator piezoelectric cylinder, whereby both cylinders can be disposed in the same cylindrical holder adapted to be employed in a wellbore or pipe. The fluid in the annular space serves as the dielectric material for the cylindrical capacitor. By measuring the capacitance, one can approximate how much liquid and gas are present since the dielectric constant of water is 80 (at room temperature) as compared to gas which is 1. If a combination of only water and gas are flowing through the apparatus, the capacitance provides a direct measure of the gas volume or the gas-fluid composition quite accurately. However, since the fluid is a combination of oil and water, and oil has a dielectric constant of approximately to 2, the fluid composition determined from the hollow cylindrical resonator, may be used to correct for the liquid present in the capacitance measurement. The temperature correction is much smaller by comparison.

Another procedure for measuring the capacitance is to add a parallel inductor to produce a resonant circuit, and to monitor the peak shift of the resonance as a function of gas composition. Any technique that measures capacitance in real time can be used.

The flow rate of fluid flowing through the piezoelectric cylinder can be determined from the frequency shift of any selected resonance peak since the entire spectrum shifts with increasing fluid flow.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, the three principal elements of an embodiment of gas separator/measurement apparatus, 10, of the present invention are illustrated. Hollow tube, 12, having axis, 14, surrounds and supports the principal elements of apparatus 10, and may either be placed in one location or moved through a pipeline or wellbore in which fluid stream, 16, of interest passes. Tube 12 may be fabricated from any sturdy and nonreactive material such as Plexiglas or metal, as examples. The first element encountered by fluid stream 14 is acoustic gas/liquid phase separator, 18, which includes piezoelectric hollow tube, 20, having exterior metal electrode, 22, and interior metal electrode, 24, deposited on the entire interior and exterior surfaces of tube 20, for electrical connection to a signal generator to be described hereinbelow. When excited by a sine wave signal at a frequency that depends on the dimensions of the piezoelectric tube, the tube undergoes low-frequency (approximately 25 kHz for a tube having an outer diameter of 4.4 cm) radial vibrations in what is known as a breathing mode. For different diameter tubes, this frequency is adjusted such that the appropriate breathing mode is generated. The impressed vibrations generate sound waves in fluid, 26, inside tube 20 from which standing waves are formed. In such standing waves, gas bubbles, 28, suspended in fluid 16 experience a differential acoustic radiation force that directs the bubbles (or gas) toward interior electrode 24 of piezoelectric tube 20. Therefore, the gas phase bubbles are directed away from axis 14 of separator 18, and the portion of fluid 26 near axis 14 with a substantial portion of the gas bubbles removed, continues to move through the center of the composition analysis element of apparatus 10.

Accurate composition measurements have been obtained even with approximately 20% by volume of gas present, provided that the gas was in the form of bubbles and were rapidly moving through the resonator tube, since the measurement is averaged over time. It is to be mentioned that 20% was found to be the maximum volume of gas through which composition measurements were able to be made with the present apparatus. The resonator tube is not always filled with gas, and the section of liquid path intercepted by the sound beam is dynamic; therefore, the resonator tube does not always experience a situation where gas is always present.

Figure 2:
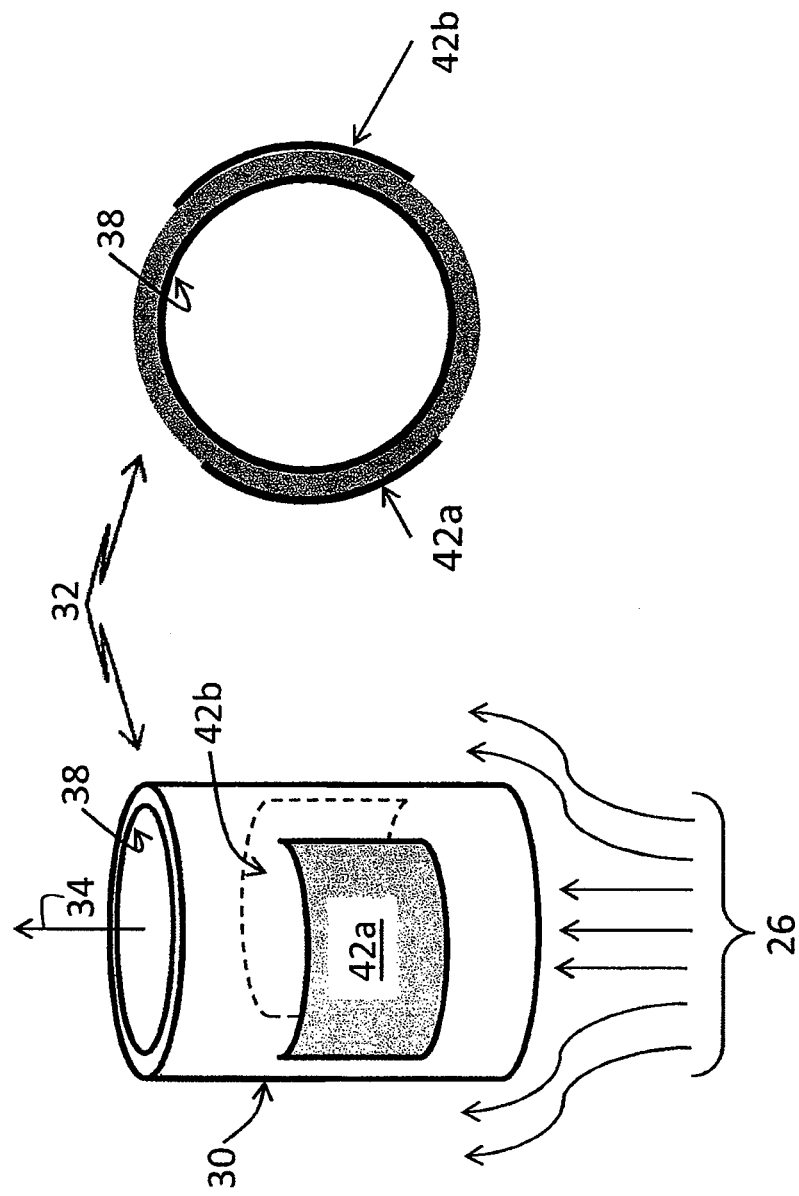
FIG. 2A is a schematic representation of a perspective view of the cylindrical resonator shown in FIG. 1A for liquid composition monitoring.
FIG. 2B is a top view thereof, illustrating the deployment of the electrodes.

Downstream from tube 20, and described in more detail in FIGS. 2A and 2B, hereof, smaller diameter and thinner-walled piezoelectric cylinder, 30, of liquid composition monitor, 32, having axis, 34, collinear with axis 14 of piezoelectric tube 20 is situated. Inside wall, 36, of cylinder 30 is completely covered with an electrode (nickel), 38, while on outside wall, 40, there are two, rectangular-shaped (1.2 cm×1.2 cm, as an example) vacuum-deposited copper or nickel electrodes, 42a, and, 42b, symmetrically positioned and diametrically aligned on opposite sides of tube 30. Piezoelectric tube 30 having two opposing transducers may now be treated in a similar fashion to a more conventional parallel plate resonator having opposing piezoelectric transducers mounted thereon, where one transducer is used as a transmitter while the other is used as a receiver. Such transducers operate in the so-called thickness resonance mode at higher operating frequencies than tube 20 (between about 1 MHz and approximately 3 MHz, depending on the thickness of the cylinder wall). With the gas phase acoustically separated from the mixed fluid phase, the determination of the oil-water ratio (composition) and the fluid flow can be more accurately made.

As will be discussed in more detail hereinbelow, by varying the frequency of the sine wave voltage applied to the transmitter electrode 42a over a range of frequencies, a large number of resonances can be observed through receiver electrode 42b as standing waves generated inside the cylinder cavity of liquid composition monitor 32. The diameter of the cylinder may vary depending on the dimensions of support tube 12, for example between about 1 cm and approximately 5 cm, although the actual dimensions are determined by the diameter of the pipe in which the fluid is flowing. The measurements set forth hereinbelow correspond to a piezoelectric material cylinder having an inner diameter of 1.7 cm, a 1 mm wall thickness, and radially polarized to have a center frequency of about 2 MHz. The external electrodes may occupy half of the cylinder surface, in which case the electrodes cover both halves of the outer surface of the cylinder, and are electrically isolated. By contrast, electrodes covering about 5% of the total surface area will also be effective for obtaining measurements. The resonance spectrum may also be observed by measuring the electrical impedance of the crystal, but the signal level is orders of magnitude smaller than that observed using the opposing transmitter-receiver electrodes illustrated in FIG. 1, where the excitation signal level is approximately 1 V peak-to-peak.

Returning to FIG. 1, gas volume measurement capacitance apparatus, 44, includes concentric metal cylinders, 46, and, 48, disposed downstream from liquid composition monitor 32, the cylinders having common axis, 50, which is collinear with axis 14, wherein central cylinder 46 is closed on both ends to prevent liquid from passing through it and disturbing the gas volume measurement. The diameter of cylinder 46 is not critical and, in an embodiment of the present apparatus, the diameter was chosen to be the same as the diameter of the piezoelectric tube resonator described hereinabove. In an embodiment of the present invention, the outer electrode was chosen to have the same diameter as the acoustic phase separator piezoelectric cylinder, whereby both cylinders can be disposed in cylindrical holder 12. The fluid in the annular space serves as the dielectric material for the cylindrical capacitor. By measuring the capacitance, since the fluid is a combination of oil and water, the fluid composition determined from the hollow cylindrical resonator, described hereinabove, may be used to correct for the liquid present in the measurement. It should be mentioned that gas volume measurement capacitance apparatus 44 may be placed upstream of acoustic gas/liquid phase separator 18, without changing the measurement functions of the elements of apparatus 10.

Figure 3:
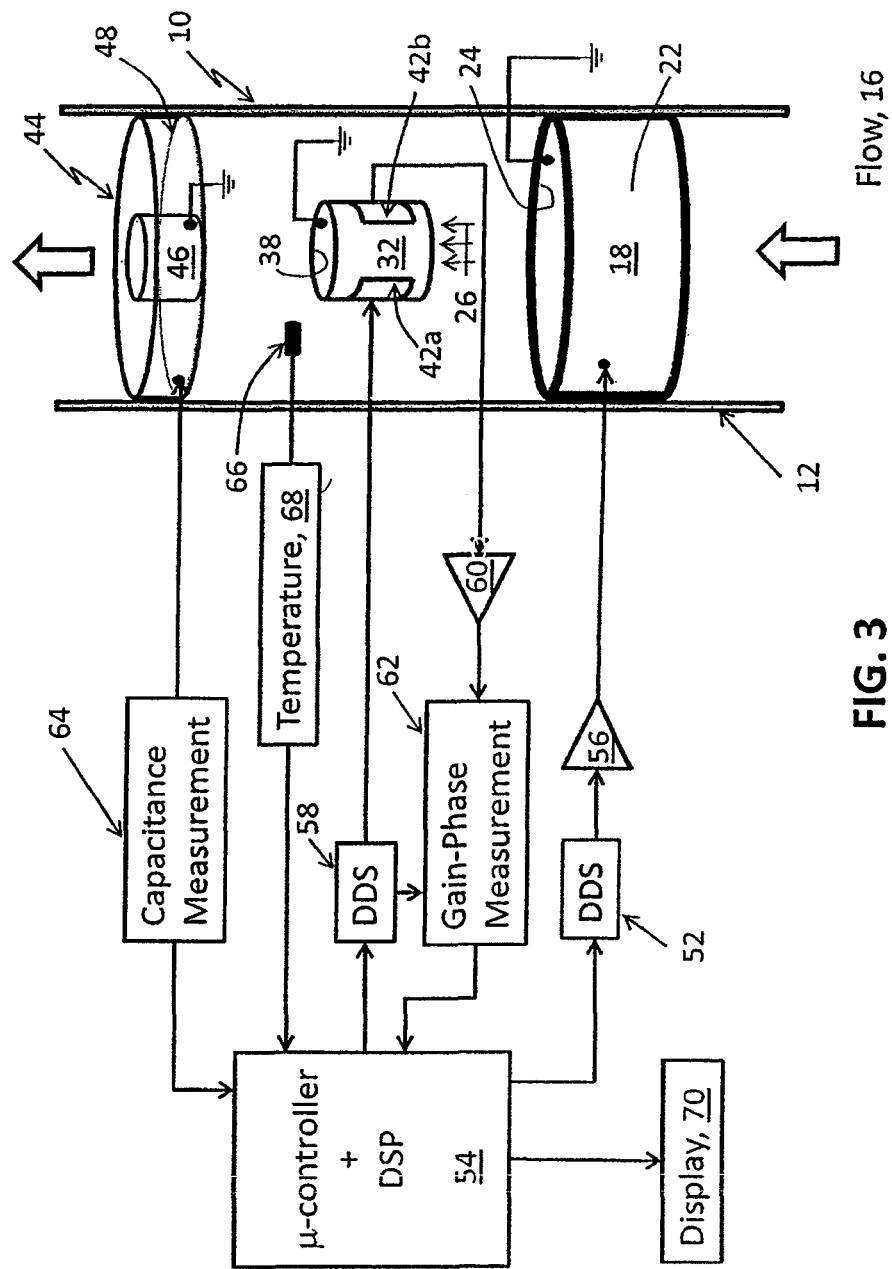
FIG. 3 illustrates the electrical components of the apparatus illustrated in FIG. 1A.

FIG. 3 is a schematic representation of an embodiment of the electronic apparatus used in cooperation with apparatus 10, where direct digital synthesizer (DDS), 52, controlled by microcontroller and digital signal processor (DSP), 54, generates a sine wave which is amplified by amplifier, 56, and directed onto one of the electrodes 22 or 24 of acoustic gas/liquid phase piezoelectric separator, 18, the other electrode being grounded. DDS, 58, triggered by microcontroller 54 generates a frequency sweep signal to one of the outer electrodes 42a on composition measurement piezoelectric cylinder 32. The output signal from second outer electrode 42b is first amplified by amplifier, 60, and directed to gain-phase measurement circuit, 62, which compares the input signal to one of the electrodes from DDS 58 to the output signal and determines the phase difference between the two signals. The amplitude of the output signal is also determined by circuit 62. The gain-phase measurement can be done in by several procedures, and the following is a general representation of the process. For example, tracking filters are not shown or described in FIG. 3. A tracking filter is used to restrict the gain phase measurement to within a very narrow band of the excitation signal for noise reduction. The combined gain-phase measurement permits more sophisticated data analyses, such as complex FFT for converting the frequency domain signal to time domain for accurate determination of sound speed in the fluid. Gain-phase circuit 54 can also be used to track a single resonance peak in a phase-locked loop configuration where the frequency from the DDS is controlled to keep the phase at a fixed value such as 0° or 90°. This is generally more reliable than controlling the excitation frequency to maintain the maximum amplitude in the output signal. Capacitance measuring, 64, device determines the capacitance of concentric cylinders 44 and directs the output thereof to microcontroller 54 for analysis.

Apparatus 10 may be approximately 13 cm, and may be lowered into a well, which permits the real-time analysis of the fluid flowing through the pipe into which apparatus 10 is inserted. Temperature measurement device, 66, and temperature recorder, 68, permit the temperature to be determined and stored, and any corrections to the data may be made using microcontroller 54 to which the output of temperature recorder 68 is directed. Results from digital signal processing in microcontroller 54 may be displayed on display, 70. While the description above relates to an oil, water and gas flow, the present invention can be used in any mixed flow where the components may be separated during flow. Additional information concerning apparatus for such analyses may be found in Patent Application Publication 20120055264 for "Apparatus and Method For Noninvasive Particle Detection Using Doppler Spectroscopy", by Dipen N. Sinha filed on 6 Sep. 2011, the entire contents of said patent application being hereby incorporated by reference herein for all that it discloses and teaches.

Having generally described embodiments of the present invention, the following EXAMPLE provides additional details.

EXAMPLE

Figure 4:
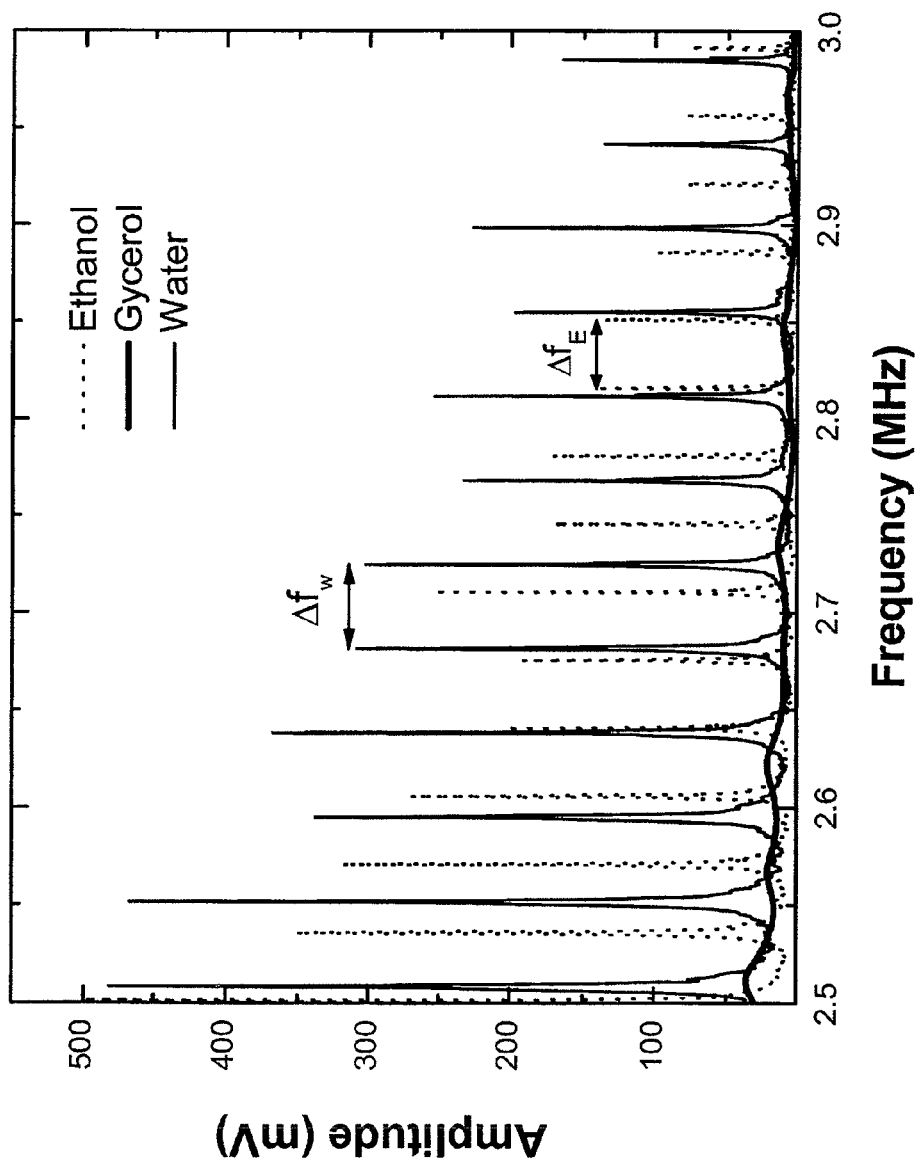
FIG. 4 shows resonance spectra for three different liquids obtained using the cylindrical resonator shown in FIG. 2A hereof, illustrating the spectral characteristics that vary with liquid, namely, the frequency difference between adjacent peaks, the width of the resonance peaks, and the change in amplitude of the peaks.

Typical resonance spectra for three liquids obtained using the cylindrical resonator are shown in FIG. 4. The spectral characteristics that vary with liquid are: (a) the frequency difference between any two adjacent peaks, (b) the width of the resonance peaks, and associated amplitude change. For the data shown, one can calculate the sound speeds for the three liquids investigated as: 1469 m/s, 1193 m/s, 1900 m/s for water, ethanol, and glycerol, respectively, which are consistent with literature values for ambient temperature within about 0.2%.

As stated hereinabove, since the geometry of the cylinder is fixed, the resonance spectrum for any given liquid is predictable. Consequently, it is possible to determine sound speed of a liquid by tracking the location of a single peak, which makes real-time monitoring of sound speed of a liquid straightforward. For a given geometry (for example, liquid path (tube diameter)), the interference pattern is well defined in the form of equally spaced resonance peaks, the spacing of which depends on the sound speed of the fluid flowing inside. For example, if the sound speed increases, the frequency spacing increases. The two components in the liquid produce two frequency patterns the peaks in each pattern being equally spaced. For any two such patterns there will be regions where the peaks will not vary significantly in frequency but there are certain frequency regions, which can be easily calculated from a sound transmission model, where the resonance peaks will be highly sensitive to sound speed variation. The exact frequency of such peaks can be related to the sound speed. Although any resonance peak may be used, sound speed is more readily monitored if peaks in the sensitive frequency region are chosen.

Another physical parameter that may be determined from such spectrum is the sound absorption, which manifests itself through the broadening of the resonance peaks. Therefore, the full-width-at-half-maximum (FWHM) of the peaks for any liquid is a measure of the sound attenuation in the liquid. The dramatic difference in this value can be easily seen from the data presented where the glycerol peaks are many times broader than that of either water or ethanol. The amplitude of a given peak is also related to the sound attenuation. Thus, two important physical parameters can be easily extracted from this resonance spectrum and these in turn can be related to the oil-water composition.

Figure 5:
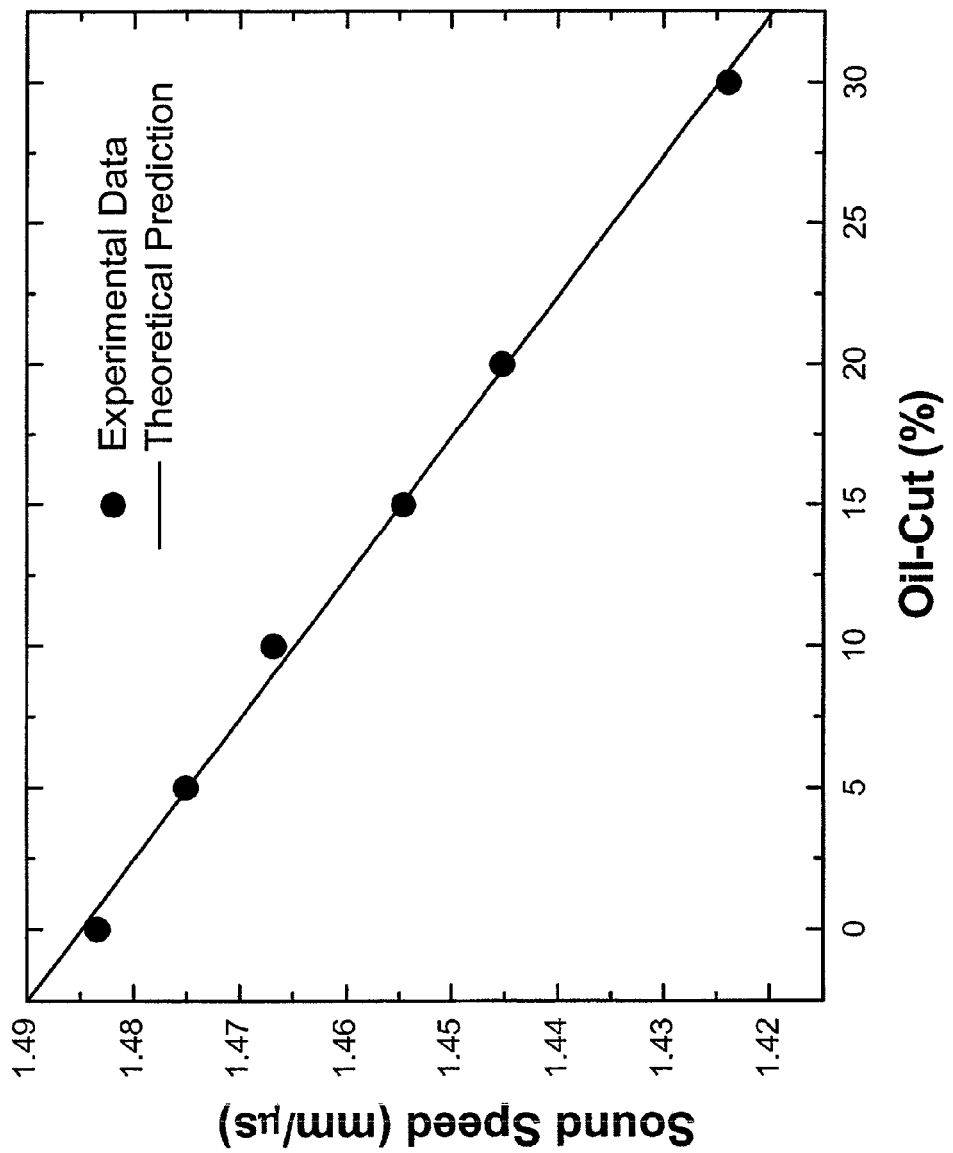
FIG. 5 shows the determination of oil-cut (the percentage of mineral oil in water) from measurement of the sound speed.

FIG. 5 illustrates the determination of oil-cut (percentage of mineral oil in water) from sound speed measurement. The theoretical prediction is derived from the following equation: $Speed_{Mixture} = \phi \cdot Speed_{Oil} + (1-\phi) \cdot Speed_{Water}$, where $\phi$ is the fluid composition. A fluid calibration is undertaken where the sound speed of both the oil and process water are separately determined by sampling the fluid and separating the oil from the water. If the individual sound speeds are known, one can determine $\phi$ from the measured sound speed of the mixture. Typically, the calibration involves the sound speed measurement over a temperature range that includes the temperature of the oil/water mixture in an operation. This permits an accurate determination of fluid mixture composition in that temperature range. There are more sophisticated forms of this mixture equation that may be employed if high accuracy (less than 1% is needed). However, the equation given is straightforward to use and is suitable for many practical applications.

As stated hereinabove, sound speed and attenuation of both crude oil and water depend on temperature. Therefore the temperature of the fluid is measured to make the appropriate corrections to the measured sound speed. As illustrated in FIG. 3 hereof, temperature measurement device 64 placed in the fluid flow inside hollow support tube 12 of apparatus 10, and recorder 66 are used to measure the temperature of fluid 26. A thermocouple, thermistor or a platinum resistance thermometer as examples, may be used to measure the temperature. The center frequency or the frequency of any structural resonance of the piezoelectric tube may also be used as a sensitive thermometer once the piezoelectric tube is calibrated. This requires an additional frequency sweep or peak tracking. To maximize the accuracy of the determination of the oil/water composition, then, corrections for variations in temperature are made using a calibration process. The sound speed and sound attenuation values are corrected over the temperature range encountered at a particular measurement site for a small sample of the crude oil being monitored, and separately for the process water that accompanies it separately. These data are then used to correct for temperature variation of the measurements. See, e.g., "The determination of the speed of sound in liquids using acoustic resonance in piezoelectric tubes", by Bogdan V. Antohe and David B Wallace, Meas. Sci. Technol. 10 (1999) 994-998, where the authors used a piezoelectric tube as a sensor and a network analyzer where the mechanical liquid loading of the tube by the liquid inside affects the electrical impedance as a small change in the total value of the electrical impedance.

Figure 6:
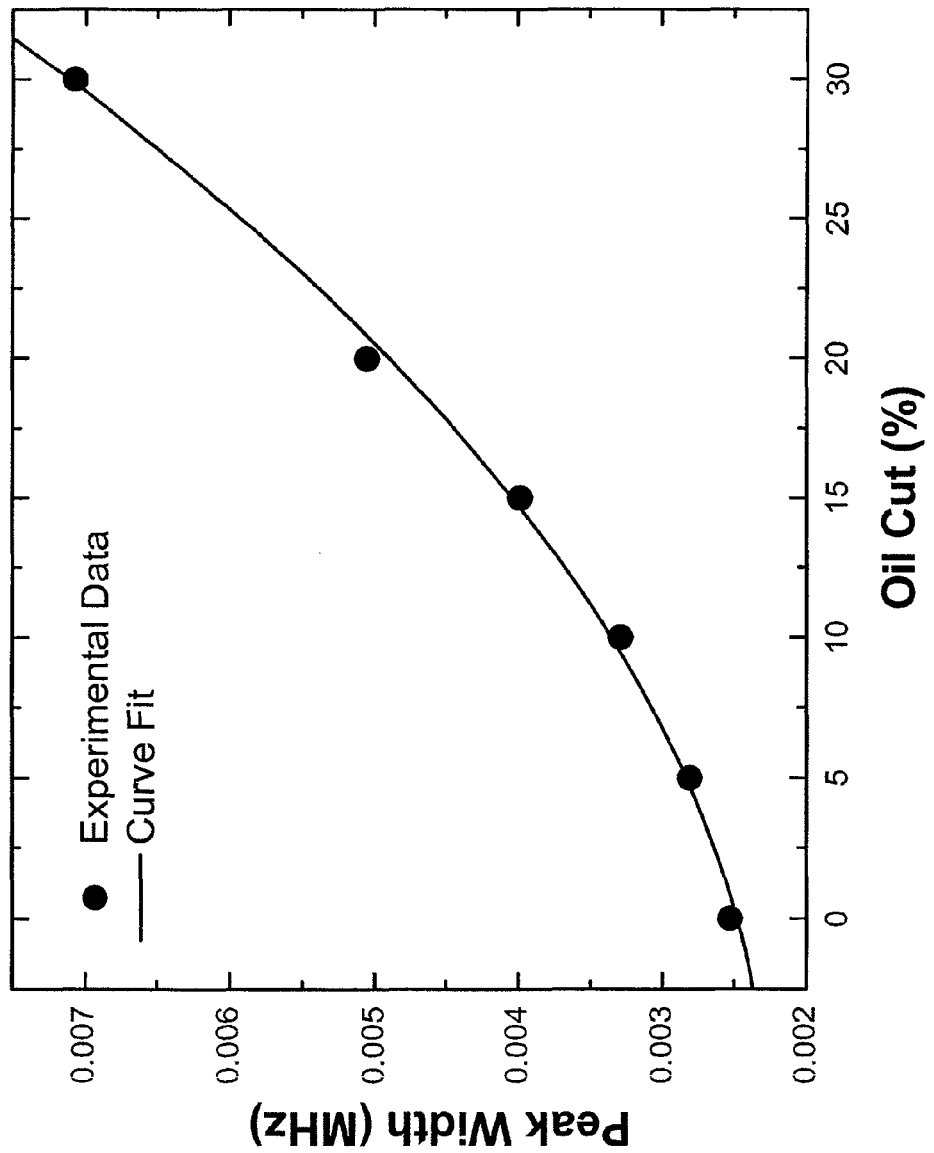
FIG. 6 shows sound attenuation as, determined from the full-width at half-maximum (FWHM) of the resonance peak, as a function of oil-cut.

As mentioned hereinabove, sound attenuation, as derived from the FWHM of the resonance peaks, is also dependent on the oil-cut (oil-water ratio). This is illustrated in FIG. 6. Although it is possible to use either sound speed or sound attenuation to determine oil-water composition, one may use both measurements for a more robust composition determination since both parameters are determined from the same resonance spectrum or peak measurement. Sound attenuation measurements are particularly sensitive for high water-cut ($\geq 70\%$) conditions, and provide a simple measurement of water-cut. Sound attenuation is also related to liquid viscosity and from Stoke's law, one can find the relationship to be proportional. Therefore, the higher the viscosity of the fluid, the higher the sound attenuation will be, and in addition to determining fluid (oil-water) composition, one can derive information concerning the quality of the oil. The measurements shown in FIGS. 5-10 were made using a piezoelectric cylinder having a diameter of 4.8 cm.

Figure 7A:
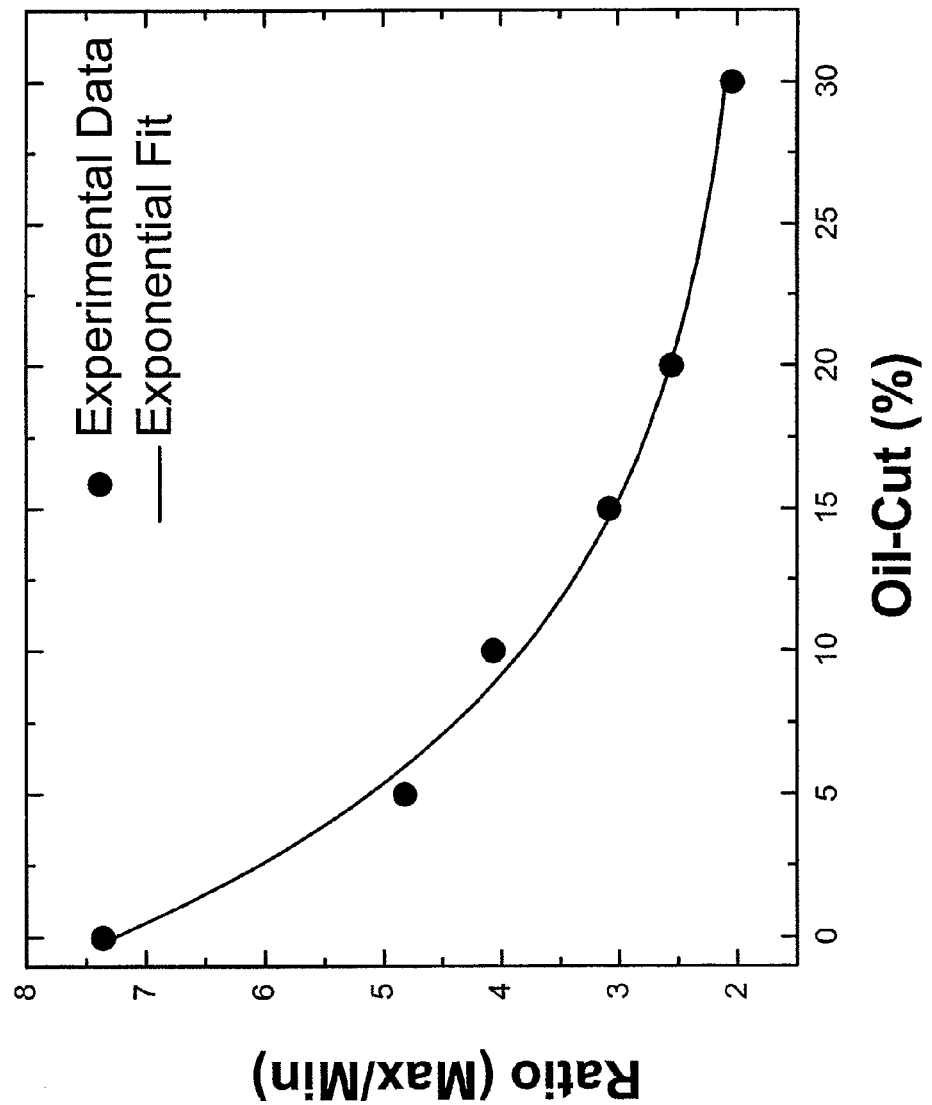
FIGS. 7A and 7B show alternate ways of analyzing sound attenuation from the resonance data in terms of the peak amplitude ($Peak_{Max}$) and the amplitude at the lowest point of the resonance curve ($Peak_{Min}$).
Figure 7B:
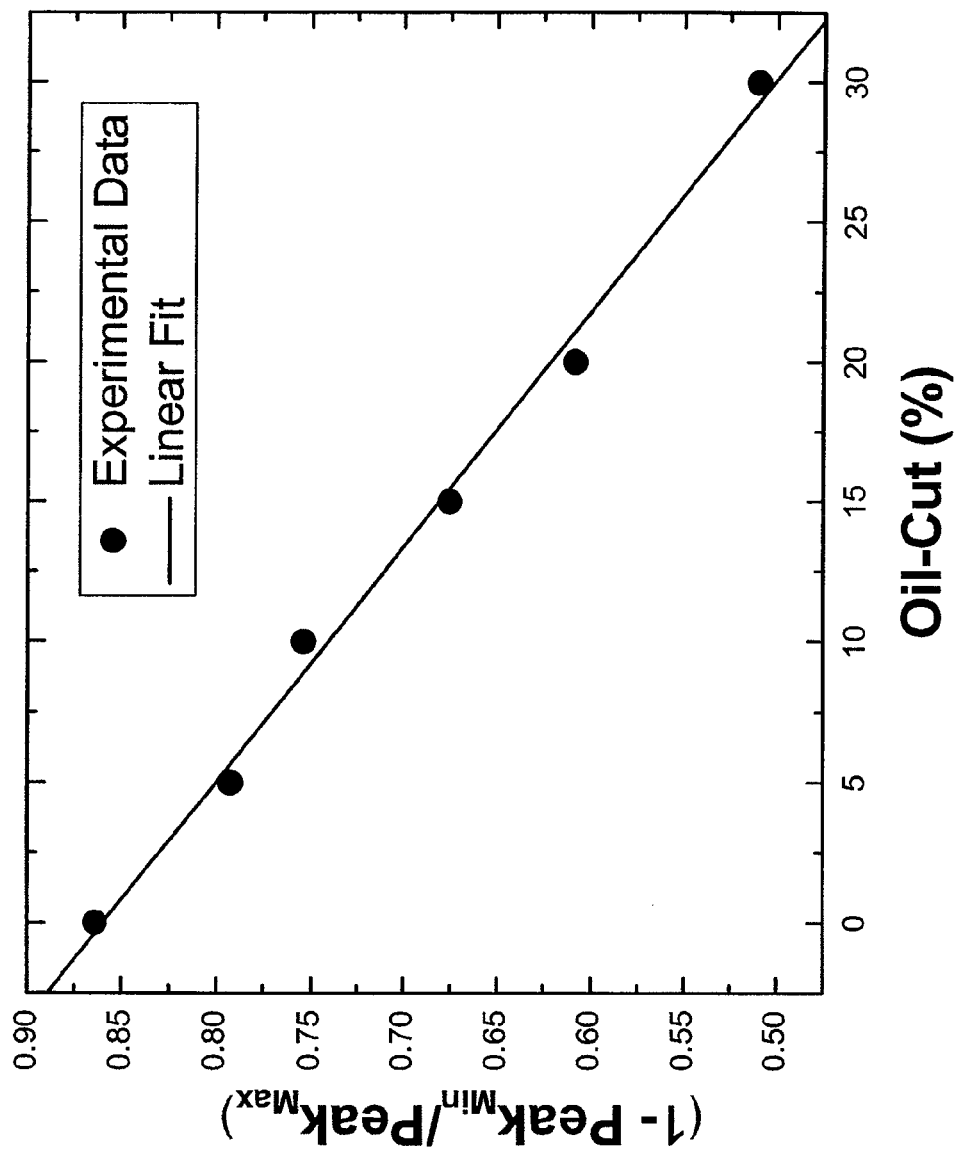

In analyzing data, it is often beneficial to determine the amplitude of a resonance peak rather than its width, which often requires a curve fitting. That is, it is equivalent to measure the peak amplitude of the resonance peak (Peak$_{Max}$) and the value at the bottom of the peak, the baseline (Peak$_{Min}$). FIG. 7A shows the ratio of these two amplitude values as a function of oil-cut, while FIG. 7B illustrates the use of the same data presented as (1−Peak$_{Min}$/Peak$_{Max}$), wherein the plot becomes a straight line which is beneficial to use as a calibration. Additional information concerning data analysis may be found in Patent Application Publication 20120055253 for "Method For Noninvasive Determination Of Acoustic Properties Of Fluids Inside Pipes", by Dipen N. Sinha et al. filed on 6 Sep. 2011, the entire contents of said patent application being hereby incorporated by reference herein for all that it discloses and teaches.

Figure 8:
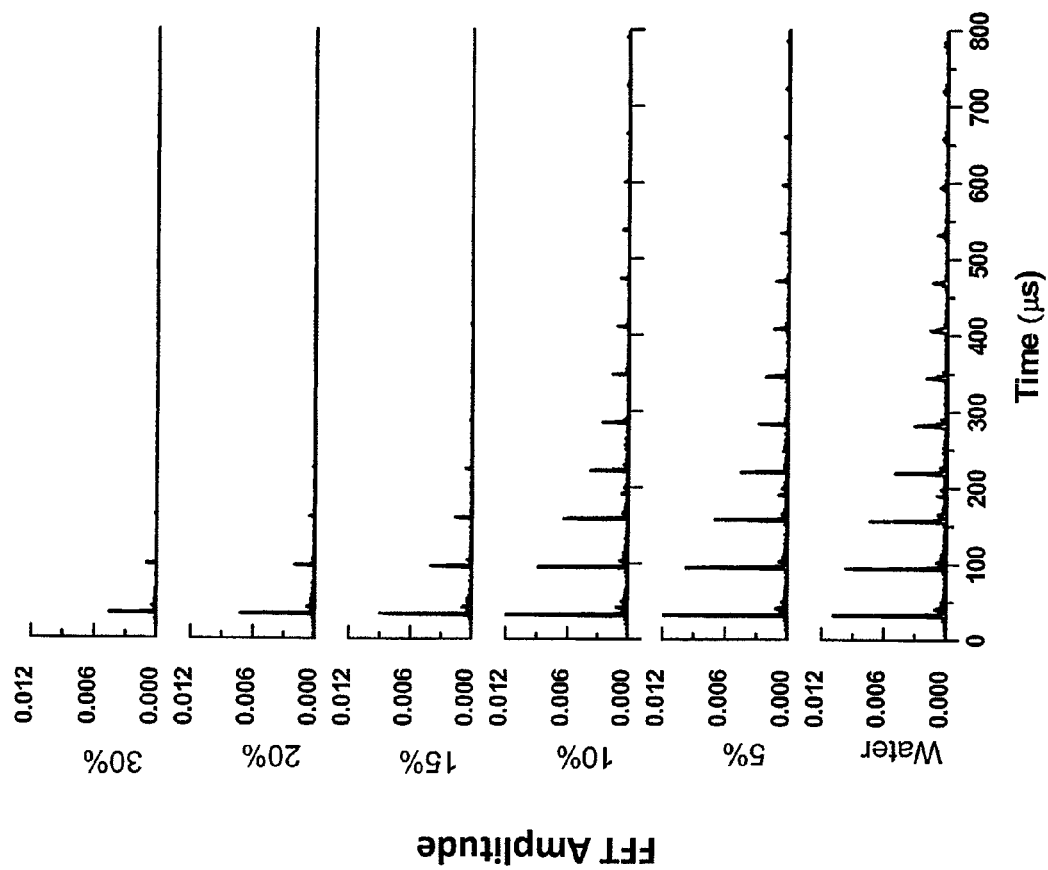
FIG. 8 shows a Fast Fourier transform (FFT) of the frequency spectrum for determining sound attenuation for six oil-cuts at high flow rate (~10 gallons/min.).
Figure 9:
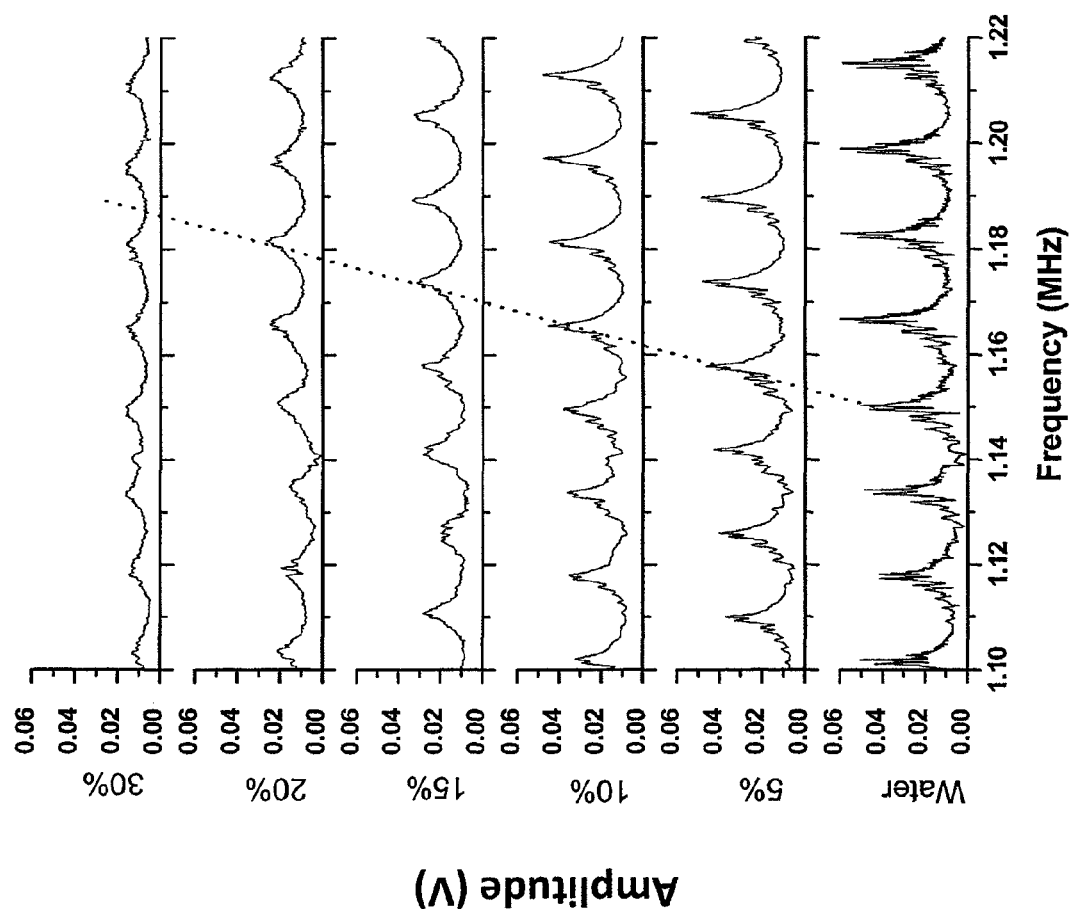
FIG. 9 shows the effect of flow on the resonance spectra for six oil cuts, illustrating the frequency shift in the resonance peaks with flow rate.

At high flow rates (for example, 20 gallons per minute), the flow becomes turbulent and the data can become noisier. It is possible to digitally filter the data to remove the noise and extract the parameters. However, by Fourier transforming the frequency spectrum (fast Fourier Transform (FFT) to the time domain, one may use the resulting time domain information for parameter extraction as shown in FIG. 8. The position of the first peak in each frame is related to the sound speed and this may be determined if the path length (the inner diameter of the piezoelectric cylinder) is known. The data in FIG. 8 also show the decay of some of the peaks decays as a function of the oil-cut; that is, at low oil-cuts, one may observe a series of peaks with progressively decreasing amplitude. As the oil-cut goes up, the rate of decay becomes more rapid and fitting the data with an exponential function and determining the decay rate provides the same information as the FWHM of the resonance peak. Theoretically, these two measurements should be identical and provide the same information. Both methods may be used.

Figure 10:
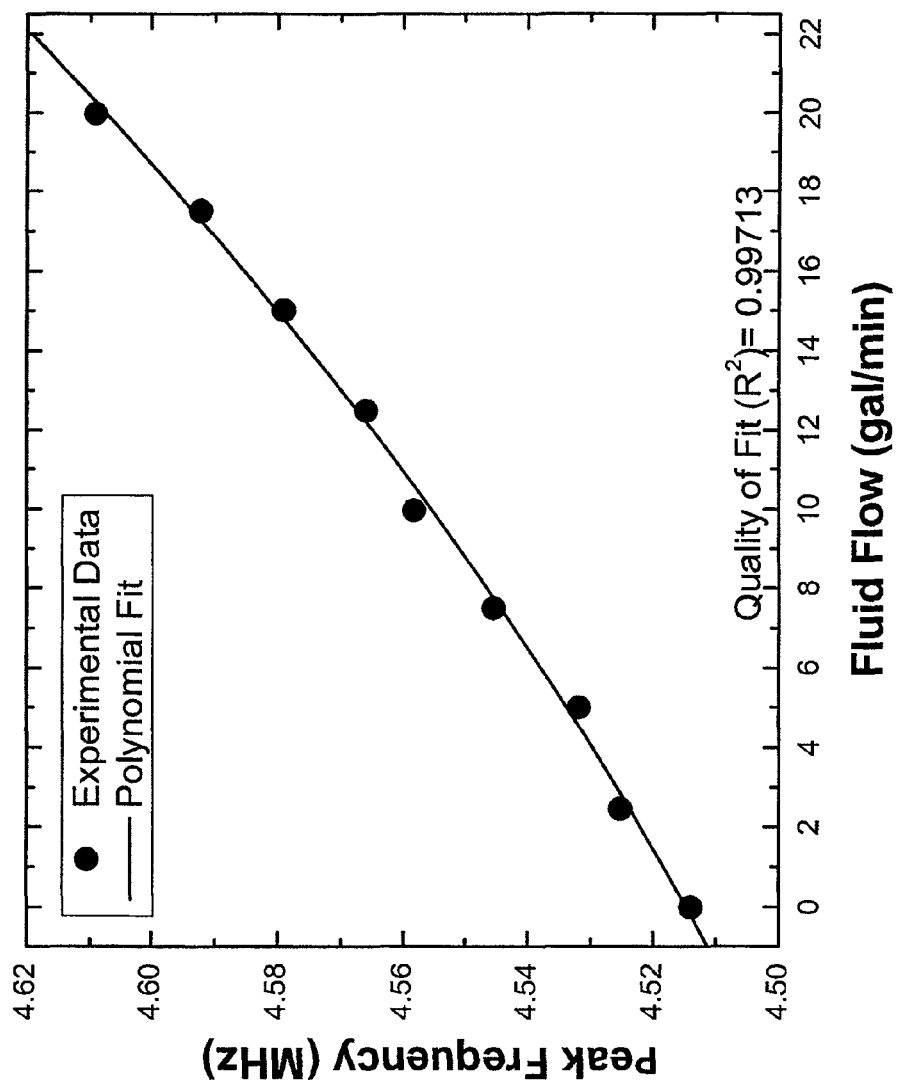
FIG. 10 shows the relationship of flow rate to the resonance peak frequency shift.

The flow rate of fluid flowing through the piezoelectric cylinder can be determined from the frequency shift of any selected resonance peak. The whole spectrum shifts with increasing fluid flow. FIG. 10 shows the measurement of flow rate and the position of an arbitrarily selected resonance peak. The data can be fitted nicely using a second order polynomial.

Figures 11A, 11B:
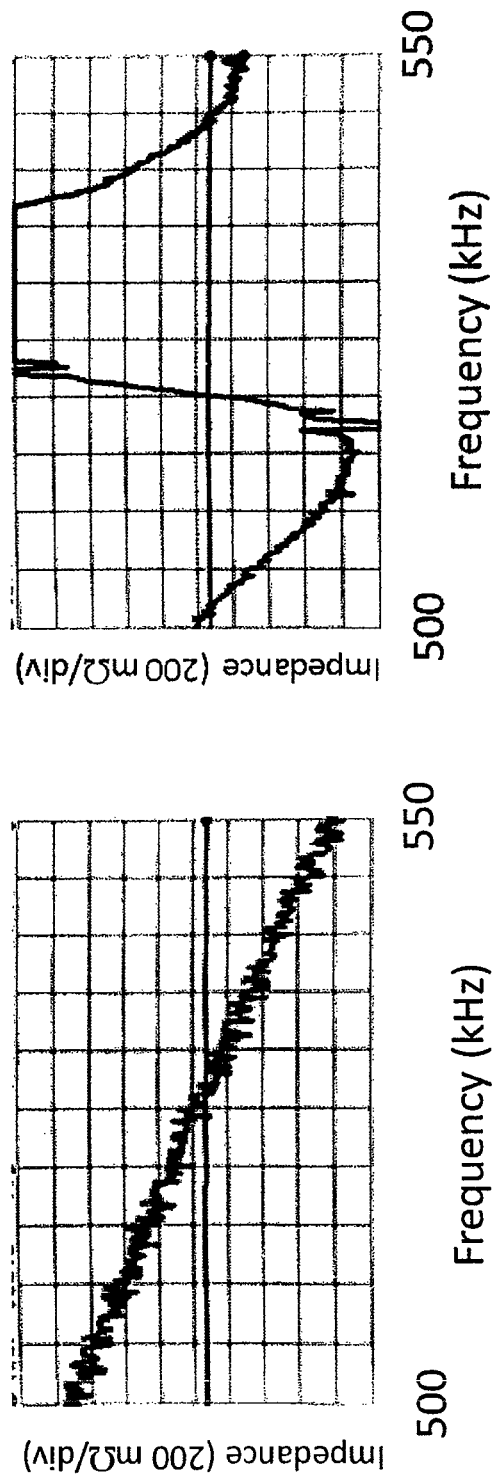

The volume of gas in the fluid may be determined by a capacitance measurement, the apparatus for which is described hereinabove as apparatus 44, and illustrated in FIGS. 1 and 3 hereof. As stated, two hollow concentric metal cylinders, a central electrode and an outer electrode are employed, with the fluid in the annular space serving as the dielectric material for the capacitor. The dielectric constant of water is 80 (at room temperature) and that of gas which is 1. If the fluid is a combination of water and gas, the capacitance measurement provides an accurate, direct measure of the gas volume of the gas-fluid composition. If the fluid is a combination of oil and water (oil having a dielectric constant of approximately 2), the fluid composition determined using liquid composition monitor 32, the hollow cylindrical resonator, is used to correct for the liquid amounts present in the measurement. Temperature corrections are much smaller by comparison. FIG. 11A shows capacitance measurements for water without bubbles as a function of time; and FIG. 11B shows capacitance measurement of water with air present. These data show the electrical impedance of the concentric capacitor when there is only liquid present when compared to the situation when liquid and gas are both present. Capacitance was measured within a narrow frequency range between about 500 and approximately 550 Hz (arbitrarily chosen). The frequency region used is not critical to the measurement, however. FIG. 11A shows the behavior of a typical capacitor where the electrical impedance varies as: Impedance=1/(2π·frequency·capacitance). Since the frequency span is small, the impedance curve is approximately a straight line. If the frequency is high, the impedance becomes small and the measurement depends on the electronics used. When gas is present, the dielectric constant of the water-gas mixture changes dramatically, as may be observed in FIG. 11B. The signal intensity exceeded the display range of the electronics employed. The geometry of the capacitor and the dielectric constant of the fluid therein determine the capacitance. A linear combination of the two media (liquid and gas) may be used to determine the volume of gas present within the volume of the capacitor.

The real-time capacitance measurement may also be made using a LC resonator circuit, where an inductor is attached in parallel with the capacitor and the resonance frequency of the LC combination is monitored. The measured resonance frequency changes with changes in capacitance.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the properties of a multiphase fluid comprising a liquid having at least one component and a gas, comprising:
   generating radial acoustic radiation forces in a first hollow piezoelectric cylinder having an axis, through which said multiphase fluid is caused to flow, such that said gas is directed away from the axis thereof and separated from said liquid;
   flowing said at least one component into a second hollow piezoelectric cylinder located coaxially with said first piezoelectric cylinder;
   generating acoustic standing waves in said at least one component; and
   measuring the frequencies and amplitudes of the acoustic standing waves from which the sound speed and sound attenuation of said at least one component from which said gas has been separated are determined;
   whereby the composition of said at least one component is determined.

2. The method of claim 1, further comprising the step of determining the temperature of the fluid.

3. The method of claim 2, further comprising the step of correcting the measured sound speed for temperature.

4. The method of claim 1, further comprising the steps of:
   remixing said liquid and said gas reforming said multiphase fluid; and
   measuring the capacitance of said multiphase fluid;
   whereby gas volume in said multiphase fluid is determined.

5. The method of claim 4, further comprising the step of flowing said multiphase fluid through an annular region between a cylindrical inner electrode and a concentric cylindrical outer electrode.

6. The method of claim 1 further comprising the step of measuring the capacitance of the multiphase fluid before said gas is directed away from the axis of the first hollow piezoelectric cylinder and separated from said liquid, whereby gas volume in the multiphase fluid is determined.

7. The method of claim 6 further comprising the step of flowing said multiphase fluid through an annular region between a cylindrical inner electrode and a concentric cylindrical outer electrode.

8. The method of claim 1, wherein said liquid having at least one component comprises oil and water; and said gas comprises at least one hydrocarbon.

9. The method of claim 1, further comprising the step of measuring the flow rate of said liquid using shifts in measured frequency of the acoustic standing waves.

* * * * *